(12) United States Patent
Hurst et al.

(10) Patent No.: US 8,557,028 B2
(45) Date of Patent: *Oct. 15, 2013

(54) BINDERLESS ZEOLITIC ADSORBENTS, METHODS FOR PRODUCING BINDERLESS ZEOLITIC ADSORBENTS, AND ADSORPTIVE SEPARATION PROCESSES USING THE BINDERLESS ZEOLITIC ADSORBENTS

(75) Inventors: Jack E. Hurst, Mobile, AL (US); Linda S. Cheng, Highland Park, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/425,774

(22) Filed: Mar. 21, 2012

(65) Prior Publication Data

US 2012/0247334 A1 Oct. 4, 2012

Related U.S. Application Data

(60) Provisional application No. 61/469,879, filed on Mar. 31, 2011.

(51) Int. Cl.
*B01D 53/02* (2006.01)
*B01J 29/06* (2006.01)

(52) U.S. Cl.
USPC .............. 95/147; 502/60; 502/67; 502/73; 502/75; 502/79; 585/800

(58) Field of Classification Search
USPC ........ 585/800; 95/147; 502/60, 67, 73, 75, 79
See application file for complete search history.

(56) References Cited

U.S. PATENT DOCUMENTS

| | | | | |
|---|---|---|---|---|
| 3,472,617 A | * | 10/1969 | Maher et al. | 423/712 |
| 4,351,981 A | | 9/1982 | Smolin | |
| 4,381,256 A | * | 4/1983 | Hildebrandt | 502/68 |
| 4,424,144 A | * | 1/1984 | Pryor et al. | 502/68 |
| 4,603,040 A | | 7/1986 | Kuznicki et al. | 423/712 |
| 4,886,929 A | * | 12/1989 | Neuzil et al. | 585/828 |
| 4,977,120 A | * | 12/1990 | Sakurada et al. | 502/64 |
| 5,403,800 A | * | 4/1995 | Beck et al. | 502/64 |
| 5,919,722 A | * | 7/1999 | Verduijn et al. | 502/66 |
| 5,993,642 A | | 11/1999 | Mohr | |
| 6,410,815 B1 | | 6/2002 | Plee | |
| 6,478,854 B1 | * | 11/2002 | Kotagiri et al. | 95/96 |
| 7,285,511 B2 | | 10/2007 | Ghosh | |
| 8,283,274 B2 | * | 10/2012 | Cheng et al. | 502/75 |
| 2005/0000860 A1 | | 1/2005 | Feng | |
| 2005/0170947 A1 | | 8/2005 | Plee | |
| 2005/0197518 A1 | | 9/2005 | Miller | |
| 2009/0326309 A1 | | 12/2009 | Priegnitz | |
| 2009/0326311 A1 | * | 12/2009 | Cheng et al. | 585/828 |
| 2010/0076243 A1 | | 3/2010 | Cheng | |
| 2010/0113854 A1 | | 5/2010 | Bouvier | |
| 2011/0011804 A1 | | 1/2011 | Cheng | |

OTHER PUBLICATIONS

Vasiliev, P. (et al.); Strong Hierarchically Porous Monoliths by Pulsed Current Processing of Zeolite Powder Assemblies; ACS Applied Materials & Interfaces, vol. 2, No. 3, pp. 732-737; published on web Feb. 10, 2010.

Miliweski, M. and Berak, J.; Effect of Adsorbent Preparation Parameters on the Selectivity for Xylene Isomers Separation; Separation Science and Technology, vol. 17, No. 2, pp. 369-374, Feb. 1982.

Morbidelli, M. (et al.); Separation of Xylenes on Y Zeolites in the Vapor Phase. 2. Breakthrough and Pulse Curves and Their Interpretation; Ind. Eng. Chem. Process Des. Dev.; vol. 24, No. 1, pp. 83-88; Jan. 1985; (ISSN 0196-4305).

Molina-Sabio, M. (et al.); Role of Chemical Activation in the Development of Carbon Porosity; Elsevier, Colloids and Surfaces A: Physicochemical and Engineering Aspects vol. 241, No. 1-3, pp. 15-25, Jul. 14, 2004.

\* cited by examiner

*Primary Examiner* — Christopher P Jones
(74) *Attorney, Agent, or Firm* — Mark R Willis

(57) ABSTRACT

Binderless BaKX zeolitic adsorbents, methods for their production, and adsorptive separation using the adsorbents are provided. An adsorbent comprises a first Zeolite X having a silica to alumina molar ratio of from about 2.0 to about 3.0; a binder-converted Zeolite X wherein a ratio of the binder-converted Zeolite X to the first Zeolite X ranges from about 10:90 to about 20:80 by weight; and barium and potassium at cationic exchangeable sites within the binderless BaKX zeolitic adsorbent. Potassium ranges from about 0.9 wt % to about 1.5 wt % and barium ranges from about 30 wt % to about 34 wt % of the binderless BaKX zeolitic adsorbent.

21 Claims, 3 Drawing Sheets

US 8,557,028 B2

BINDERLESS ZEOLITIC ADSORBENTS, METHODS FOR PRODUCING BINDERLESS ZEOLITIC ADSORBENTS, AND ADSORPTIVE SEPARATION PROCESSES USING THE BINDERLESS ZEOLITIC ADSORBENTS

CROSS-REFERENCE TO RELATED APPLICATION

This application claims the benefit of U.S. Provisional Application No. 61/469,879 filed on Mar. 31, 2011.

FIELD OF THE INVENTION

The present invention generally relates to zeolitic adsorbents, methods for making the adsorbents, and selective adsorptive separation processes using the adsorbents. More particularly, the invention relates to binderless BaKX zeolitic adsorbents, methods for their production, and methods of recovering para-xylene from mixed xylenes in selective adsorptive separation processes using binderless BaKX zeolitic adsorbents.

DESCRIPTION OF RELATED ART

The simulated moving bed (SMB) adsorption process is used commercially in a number of large scale petrochemical separations to recover high purity para-xylene from mixed xylenes. As used herein, "mixed xylenes" refers to a mixture of C8 aromatic isomers that includes ethyl benzene, para-xylene, meta-xylene, and ortho-xylene. High purity para-xylene is used for the production of polyester fibers, resins and films. Para-xylene typically is converted to terephthalic acid or dimethyl terephthalate, which is then reacted with ethylene glycol to form polyethylene terephthalate, the raw material for most polyesters.

The general technique employed in the performance of simulated moving bed adsorptive separation processes is widely described and practiced. Generally, the process simulates a moving bed of adsorbent with continuous counter-current flow of a liquid feed over the adsorbent. Feed and products enter and leave adsorbent beds continuously, at nearly constant compositions. Separation is accomplished by exploiting the differences in affinity of the adsorbent for para-xylene relative to the other C8 aromatic isomers.

Typical adsorbents used in simulated moving bed adsorption processes generally include crystalline aluminosilicate zeolites and can comprise both the natural and synthetic aluminosilicates. Suitable crystalline aluminosilicate zeolites for use as an adsorbent selective for para-xylene include those having aluminosilicate cage structures in which alumina and silica tetrahedra are intimately connected with each other in an open three dimensional crystalline network. The tetrahedra are cross linked by the sharing of oxygen atoms, with spaces between the tetrahedra occupied by water molecules prior to partial or total dehydration of the zeolite. The dehydration results in crystals interlaced with channels having molecular dimensions. In a hydrated form the crystalline aluminosilicate zeolites are generally represented by the formula: $M_{2/n}O:Al_2O_3:wSiO_2:yH_2O$ where "M" is a cation that balances the electrovalence of the tetrahedra and is generally referred to as an exchangeable cationic site, "n" represents the valence of the cation, "w" represents the moles of $SiO_2$, and "y" represents the moles of water. Such crystalline aluminosilicate zeolites that find use as an adsorbent possess relatively well-defined pore structures. The exact type aluminosilicate zeolite is generally identified by the particular silica:alumina molar ratio and the pore dimensions of the cage structures.

Cations (M) occupying exchangeable cationic sites in the zeolitic adsorbent may be replaced with other cations by ion exchange methods well known to those having ordinary skill in the field of crystalline aluminosilicates. Crystalline aluminosilicates, such as Zeolite X with barium and potassium cations at the exchangeable cationic sites within the zeolite, are known to selectively adsorb para-xylene in a mixture comprising at least one other C8 aromatic isomer.

Generally, zeolitic adsorbents used in separative processes contain the zeolitic crystalline material dispersed in an amorphous material or inorganic matrix, having channels and cavities therein which enable liquid access to the crystalline material. Silica, alumina or certain clays and mixtures thereof are typical of such inorganic matrix materials, which act as a "binder" to form or agglomerate the zeolitic crystalline particles that otherwise would comprise a fine powder. Agglomerated zeolitic adsorbents may thus be in the form of particles such as extrudates, aggregates, tablets, macrospheres such as beads, granules, or the like.

The binder is typically inert and does not contribute to any selective adsorption. Efforts have been made to improve adsorbent productivity by increasing the selective part (zeolite volume) within adsorbents by converting the binder into selective zeolite in a conversion process referred to as "zeolitization", while maintaining the strength and macroporosity of the zeolitic adsorbent. This conversion process results in a "binderless" zeolitic adsorbent. While this conversion process has resulted in an increase in adsorbent productivity, still further increases in process performance and decreases in operating costs for adsorptive separation processes are sought.

Accordingly, it is desirable to provide a binderless adsorbent and methods to recover high purity para-xylene from a feed mixture having at least one other C8 aromatic isomer in an adsorptive separation process using the binderless adsorbent so that process performance is improved and operating costs are lowered. In addition, it is desirable to provide a binderless BaKX zeolitic adsorbent that decreases the amount of adsorbent and desorbent required to process a fixed amount of feed. It is also desirable to provide a method for forming such a binderless adsorbent. Furthermore, other desirable features and characteristics of the present invention will become apparent from the subsequent detailed description of the invention and the appended claims, taken in conjunction with the accompanying drawings and this background of the invention.

SUMMARY OF THE INVENTION

The present invention provides a binderless BaKX zeolitic adsorbent, a method for producing the binderless BaKX zeolitic adsorbent, and a process for adsorptive separation of para-xylene from a feed mixture comprising at least one other C8 aromatic isomer using the binderless BaKX zeolitic adsorbent. In an embodiment, the invention is a binderless BaKX zeolitic adsorbent comprising: a first Zeolite X having a silica to alumina molar ratio of from about 2.0 to about 3.0; a binder-converted Zeolite X wherein a ratio of the binder-converted Zeolite X to the first Zeolite X ranges from about 1 to 9 to about 1 to 4 by weight; and barium and potassium at cationic exchangeable sites within the binderless BaKX zeolitic adsorbent, wherein an amount of potassium ranges from about 0.9 wt % to about 1.5 wt % of the binderless BaKX zeolitic adsorbent, and an amount of barium ranges from about 30 wt % to about 34 wt % of the binderless BaKX zeolitic adsorbent.

In another embodiment, the invention is a method for producing a binderless BaKX zeolitic adsorbent comprising: forming agglomerates having ion-exchangeable sites, the agglomerates formed from Zeolite X having a silica to alumina molar ratio of from about 2.0 to about 3.0, a kaolin clay binder, and carboxymethyl cellulose. The agglomerates are activated to convert the kaolin clay binder to meta-kaolin clay binder and the meta-kaolin clay binder is converted into a binder-converted Zeolite X. The carboxymethyl cellulose is dissipated. The ion-exchangeable sites are exchanged with barium and potassium to provide the binderless BaKX zeolitic adsorbent wherein potassium is present in an amount ranging from about 0.9 wt % to about 1.5 wt % of the binderless BaKX zeolitic adsorbent, and barium is present in an amount ranging from about 30 wt % to about 34 wt % of the binderless BaKX zeolitic adsorbent; and the binderless BaKX zeolitic adsorbent is dried.

In a further embodiment, the invention is a process for separating para-xylene from a feed mixture comprising at least one other C8 aromatic isomer. The process comprises: contacting the feed mixture with a binderless BaKX zeolitic adsorbent comprised of a first Zeolite X portion having a silica to alumina molar ratio of from about 2.0 to about 3.0; a binder-converted Zeolite X portion; and barium and potassium at cationic exchangeable sites within the binderless BaKX zeolitic adsorbent, wherein potassium is present in an amount ranging from about 0.9 wt % to about 1.5 wt % of the binderless BaKX zeolitic adsorbent, and barium is present in an amount ranging from about 30 wt % to about 34 wt % of the binderless BaKX zeolitic adsorbent. Para-xylene is caused to be adsorbed on the binderless BaKX zeolitic adsorbent. A less selectively adsorbed portion of the feed mixture is removed from contact with the binderless BaKX zeolitic adsorbent as a raffinate stream; and the para-xylene is recovered from the binderless BaKX zeolitic adsorbent by desorption with a desorbent.

DETAILED DESCRIPTION

Figure 1:
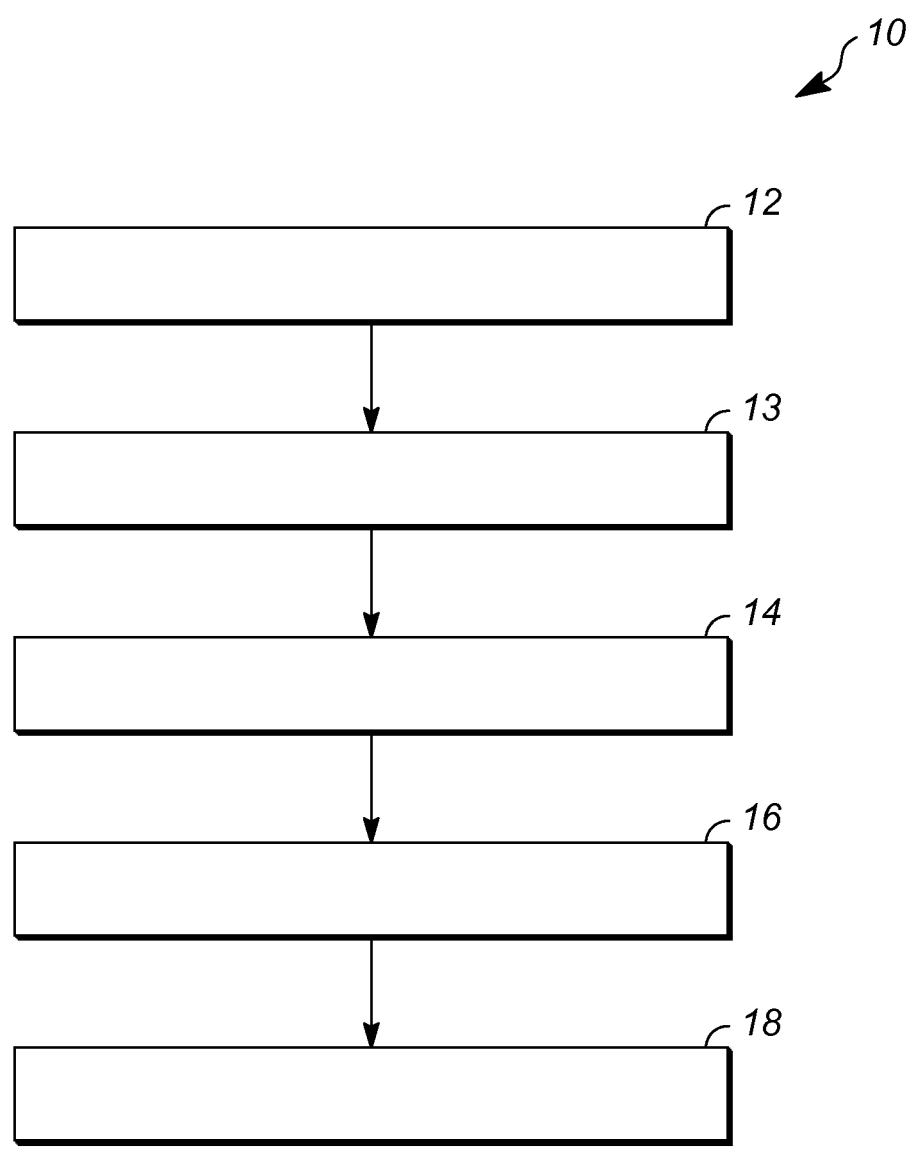
FIG. 1 is a flow chart of methods of producing a binderless BaKX zeolitic adsorbent according to exemplary embodiments of the present invention.

The following detailed description of the invention is exemplary in nature and is not intended to limit the invention or the application and uses of the invention. Also, there is no intention to be bound by any theory presented in the preceding background of the invention or the following detailed description of the invention.

In accordance with exemplary embodiments of the present invention, a binderless BaKX zeolitic adsorbent comprises a first portion of Zeolite X having a silica to alumina ($SiO_2$/$Al_2O_3$) molar ratio of from about 2.0 to about 3.0 and a second portion of Zeolite X being a binder-converted Zeolite X. The ratio of the binder-converted portion of Zeolite X to the first portion of Zeolite X ranges from about 10:90 to about 20:80 by weight. That is, the binder-converted Zeolite X is formed from x weight percent (wt %) inert clay binder, wherein x is in the range of about 10 wt % to about 20 wt % of the binderless BaKX zeolitic adsorbent, and the first portion of Zeolite X is (100-x) wt % of the binderless BaKX zeolitic adsorbent. In an embodiment, the ratio of the binder-converted Zeolite X to the first Zeolite X ranges from about 14:86 to about 18:82 by weight.

Barium (Ba) and potassium (K) are at cationic exchangeable sites within the binderless BaKX zeolitic adsorbent, with the potassium in the range of about 0.9% to about 1.5% by weight and the barium ranging from about 30% to about 34% by weight of the binderless BaKX zeolitic adsorbent. Further, the inert clay binder and the first Zeolite X may be mixed with carboxymethyl cellulose prior to formation of the binder-converted zeolite portion. The amount of carboxymethyl cellulose ranges from more than 0 to about 5 wt % of the combined weight of the inert clay binder and the first Zeolite X. As used herein, the weights and weight percentages of first Zeolite X, binder-converted Zeolite X, inert clay binder, potassium, barium, and sodium are on a volatile-free basis, i.e. after accounting for losses during the LOI test described hereinafter. Although the amount of carboxymethyl cellulose is determined from the volatile free weights of the first Zeolite X and inert clay binder, no adjustment is made to the amount of carboxymethyl cellulose itself to account for losses during the LOI test because substantially all of the carboxymethyl cellulose would dissipate at 900° C. In an embodiment, the pore volume of the binderless BaKX zeolitic adsorbent measured by Hg intrusion porosimetry is between about 0.25 cc/g and 0.35 cc/g.

According to exemplary embodiments of the present invention, Zeolite X comprises a specific crystalline aluminosilicate zeolite for use in the adsorbent. In hydrated form, Zeolite X can be represented in terms of mole oxides as follows:

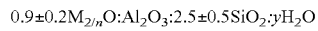

$$0.9\pm0.2M_{2/n}O:Al_2O_3:2.5\pm0.5SiO_2:yH_2O$$

where "M" is at least one cation having a valence of not more than 3, which balances the electrovalence of the tetrahedra and is generally referred to as an exchangeable cationic site, "n" represents the valence of the cation, and "y" represents the moles of water (y is a value up to about 9 depending upon the identity of M and the degree of hydration of the crystalline). Zeolite X possesses a relatively well-defined pore structure. As the Zeolite X is initially prepared, the cation "M" is usually predominately sodium and thus is referred to as a sodium-type Zeolite X. The defined $SiO_2$/$Al_2O_3$ mole ratio of Zeolite X is in the range of about 2.5±0.5. In an embodiment, the first Zeolite X has a silica to alumina molar ratio in the range of about 2.3 to about 2.7, and optionally is about 2.5.

FIG. 1 is a flow chart of a method 10 for preparing the binderless BaKX zeolitic adsorbent in accordance with an exemplary embodiment. The method begins with the formation of adsorbent agglomerates (step 12) comprised of Zeolite X and inert binder. The Zeolite X is agglomerated into adsorbent beads using the inert binder by mixing at ambient temperature with water. In an embodiment, the inert binder comprises kaolin clay with a silica:alumina molar ratio in the range of about 2.0 to about 2.2. Kaolin clay is available, e.g. from Imerys with a North American Corporate Office in Roswell, Ga. and U.S. Silica Co. in Berkeley Springs, W. Va. The beads may be comprised of from about 80 to about 90 wt % of Zeolite X and about 10 to about 20 wt % of kaolin clay binder on a volatile-free basis. The kaolin clay binder holds the starting zeolite powder together to form adsorbent beads with a particle size in the range of about 0.3 mm to about 0.8 mm. While agglomerates in the form of beads have been described, the invention is not so limited. The Zeolite X and binder may be formed into other shaped particles such as extrudates, aggregates, tablets, macrospheres, granules, or the like by aggregation and/or other well known processes in the art of making adsorbents and catalysts, including, compaction and extrusion.

In an exemplary embodiment, additives such as polymers and fibers may also be mixed with the Zeolite X and inert binder during the agglomerate-forming step 12. For example, carboxymethyl cellulose may be added in a positive amount, i.e. more than 0, up to about 5.0 wt % of the total, combined, volatile-free, weights of the inert binder and the starting Zeolite X.

To convert the kaolin clay binder to a binder-converted Zeolite X, the agglomerates are activated at a temperature ranging from about 625° C. to about 700° C. to convert the kaolin clay binder into meta-kaolin clay binder (step 13). The kaolin clay binder undergoes an endothermic dehydroxylation reaction and converts to a disordered meta-kaolin phase. If carboxymethyl cellulose was previously added, it may be dissipated, i.e. burnt off, during this step.

Next, the meta-kaolin clay binder is then caustic-digested at a temperature of about 80° C. by a sodium hydroxide solution and the meta-kaolin binder is converted to binder-converted Zeolite X having a silica:alumina molar ratio in the range of from about 2.0 to about 2.2 (step 14). For 1 g of meta-kaolin clay binder, about 41 g of 2.4 wt % NaOH is needed for conversion. The conversion results in about a 15% increase in selective pore volume as determined through McBain $O_2$ capacity measurements at liquid $O_2$ temperature. Such measurement is described in "Zeolite Molecular Sieves: Structure, Chemistry and Use" by Donald W. Breck, John Wiley & Sons, 1974. In exemplary binderless zeolitic adsorbents, non-zeolitic material is substantially absent, i.e. non-zeolitic material is present in the adsorbent generally in an amount of less than about 2% by weight, typically less than 1% by weight, and often less than 0.5% by weight. The absence or substantial absence of non-zeolitic or amorphous material may be confirmed by analysis of the binderless adsorbent using X-ray diffraction and/or high resolution scanning electron microscopy (HR-SEM) to verify crystal structure.

In an embodiment, the adsorbent beads comprise a first Zeolite X portion (from the starting already made or prepared Zeolite X) having a silica to alumina molar ratio in the range of about 2.5±0.5, optionally about 2.5, and the binder-converted Zeolite X portion (from the inert binder) with a silica:alumina molar ratio in the range of about 2.0 to about 2.2. In another embodiment, the first Zeolite X has a silica to alumina molar ratio in the range of about 2.3 to about 2.7, and the binder-converted Zeolite X has a silica to alumina molar ratio in the range of about 2.0 to about 2.2.

While the conversion of a kaolin clay binder to binder-converted Zeolite X has been described, the invention is not so limited. For example, other clay binders may be converted to a binder-converted Zeolite X. Non-limiting examples include clays belonging to the halloysite family. In addition, while the use of a sodium hydroxide solution has been described as the caustic solution for binder conversion, the invention is not so limited. In addition to sodium hydroxide, other aqueous alkali metal hydroxide solutions may be used for conversion. Non-limiting examples include a solution of potassium hydroxide or a mixture of sodium hydroxide and potassium hydroxide The binderless zeolitic adsorbent beads are then exposed to $Ba^{2+}$ cations and $K^+$ cations for ion-exchange to produce the "binderless BaKX zeolitic adsorbent" (step 16). In a preferred embodiment, substantially all of the ion-exchangeable sodium (Na) sites of the binderless zeolitic adsorbent beads are exchanged with barium and potassium such that the weight percent of sodium in the binderless BaKX zeolitic adsorbent is less than about 0.15%, and may be less than about 0.10% (on a volatile free basis). The barium and potassium ions are exchanged in relative amounts so that potassium will be in the range of about 0.9% to about 1.5% and barium will be in the range of about 30% to about 34%, by weight on a volatile free basis relative to the weight of the binderless BaKX zeolitic adsorbent. Optionally, the amount of barium ranges from about 31 wt % to about 33 wt % of the binderless BaKX zeolitic adsorbent.

In another embodiment, the potassium content of the binderless BaKX zeolitic adsorbent ranges from more than 0.9 wt % to about 1.25 wt %; optionally the amount of potassium ranges from about 0.95 wt % to about 1.15 wt % of the binderless BaKX zeolitic adsorbent and the amount of barium ranges from about 31 wt % to about 33 wt % of the binderless BaKX zeolitic adsorbent.

In one exemplary embodiment, the exchange can be in a single step with a mixture of barium and potassium such that the weight percentages of barium and potassium in the binderless BaKX zeolitic adsorbent will be in the above-mentioned ranges. Alternatively, the exchanges may take place sequentially, with each step exchanging an appropriate amount of ions to produce a binderless BaKX zeolitic adsorbent having weight percentages of barium and potassium ions in the above-described ranges. The single step and alternative sequential step exchange are identified collectively in FIG. 1 as step 16. While the ion exchange is described as occurring after agglomeration of the Zeolite X and after conversion, the invention is not so limited. The exchange with barium and potassium may occur prior to agglomeration of the Zeolite X or after forming agglomerates and before conversion, but some ion exchange after conversion may still be required as sodium hydroxide is used to convert the meta-kaolin to zeolite. Cation exchange capacity calculations in Zeolite X are described in "Zeolite Molecular Sieves: Structure, Chemistry, and Use" by Donald W. Breck, John Wiley & Sons, 1974.

Next, the binderless BaKX zeolitic adsorbent is dried to fix its water content (step 18). In this regard, the binderless BaKX zeolitic adsorbent is activated by washing and drying the beads to about 4 to about 7% Loss on Ignition (LOI at 900° C.). The drying is generally carried out by thermal activation, preferably at temperatures of from about 175° C. to about 250° C. The water content of the adsorbent is expressed herein in terms of the recognized LOI test at 900° C. The LOI test is described in UOP Test Method No. UOP954-03 (available through ASTM International, 100 Barr Harbor Drive, PO Box C700, West Conshohocken, Pa., 19428-2959 USA).

As noted above, carboxymethyl cellulose may be added to the Zeolite X and the clay binder mixture during the bead-forming stage. The addition of carboxymethyl cellulose increases the meso- and macro-porosity of the adsorbent beads. As used herein and conventionally, "macro-pores" are defined as pores having a pore diameter greater than 50 nm and "meso-pores" are defined as pores having a pore diameter between 2 and 50 nm. Macro- and meso-porosity facilitates conversion of the binder by permitting the sodium hydroxide conversion solution to flow throughout the binder. The macro- and meso-pores also help improve the mass transfer rate of the binderless BaKX zeolitic adsorbent. Mercury Intrusion Porosimetry as described in UOP Test Method No.

UOP578-02 (available through ASTM International, 100 Barr Harbor Drive, PO Box C700, West Conshohocken, Pa., 19428-2959 USA) may be used to quantify macro-pores and meso-pores, but not micro-pores.

The binderless BaKX zeolitic adsorbents, according to the present invention, may be used in various types of well known adsorptive separation processes for the recovery of para-xylene from a mixture comprising at least one other C8 aromatic isomer. Non-limiting examples include: batch and continuous operating modes; liquid phase and gas phase operations; fix-bed, moving bed, and simulated moving bed operations; and counter-current and co-current flows. In an exemplary embodiment, the binderless BaKX zeolitic adsorbent is used in counter-current, liquid phase, simulating moving bed, adsorptive separation processes for the recovery of para-xylene from mixed xylenes. The adsorbents are selective for para-xylene.

Figure 2:
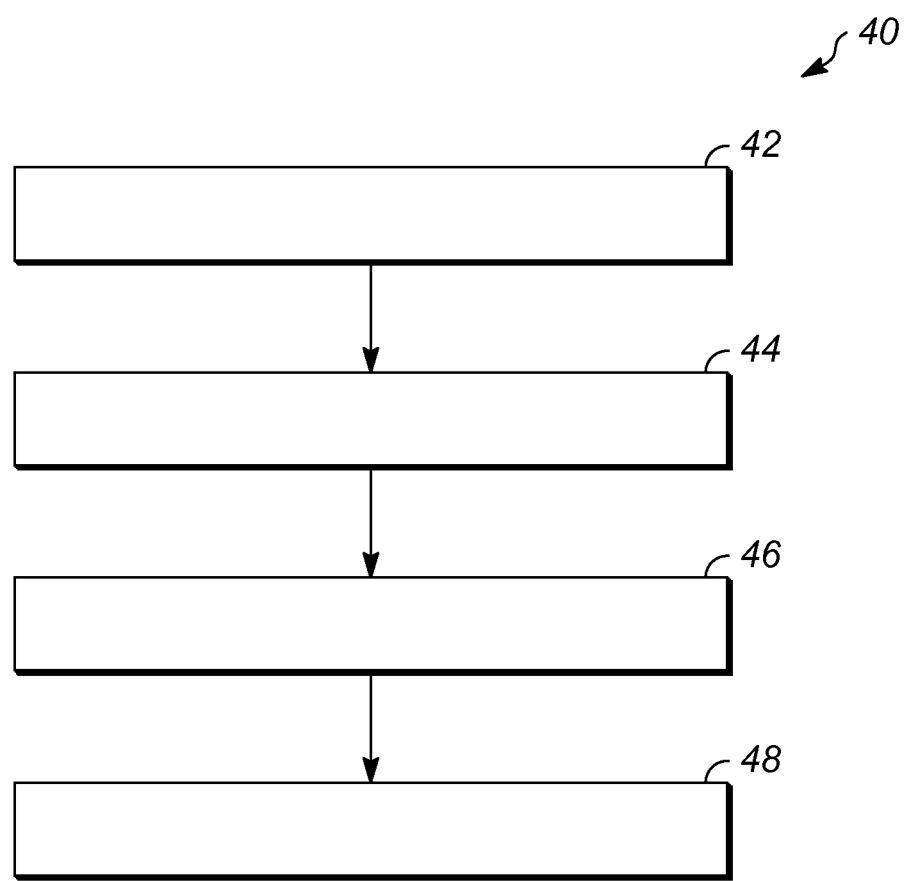
FIG. 2 is a flow chart illustrating the process steps for use of the binderless BaKX zeolitic adsorbent in the adsorptive separation unit of FIG. 3 in accordance with exemplary embodiments of the present invention.

In an embodiment as shown in FIG. 2, the process 40 comprises contacting the mixed xylenes feed at liquid phase adsorption conditions with a binderless BaKX zeolitic adsorbent (step 42), causing para-xylene to be adsorbed on the binderless BaKX zeolitic adsorbent (step 44), causing a less selectively adsorbed portion of the feed mixture to be removed from contact with the binderless BaKX adsorbent as a raffinate stream (step 46), and purifying and recovering the para-xylene by desorption with a desorbent at desorption conditions (step 48). The desorbent displaces the para-xylene from the adsorbent. Adsorption conditions can include a temperature range of from about 148° C. to about 177° C., and a pressure range of from about atmospheric to about 3447 KPa. In an embodiment, the adsorption conditions include pressures and temperatures as required to ensure liquid phase operation. Preferred cycle times are 20-34 minutes. Desorption conditions may include the same temperature and pressure as used for adsorption.

Figure 3:
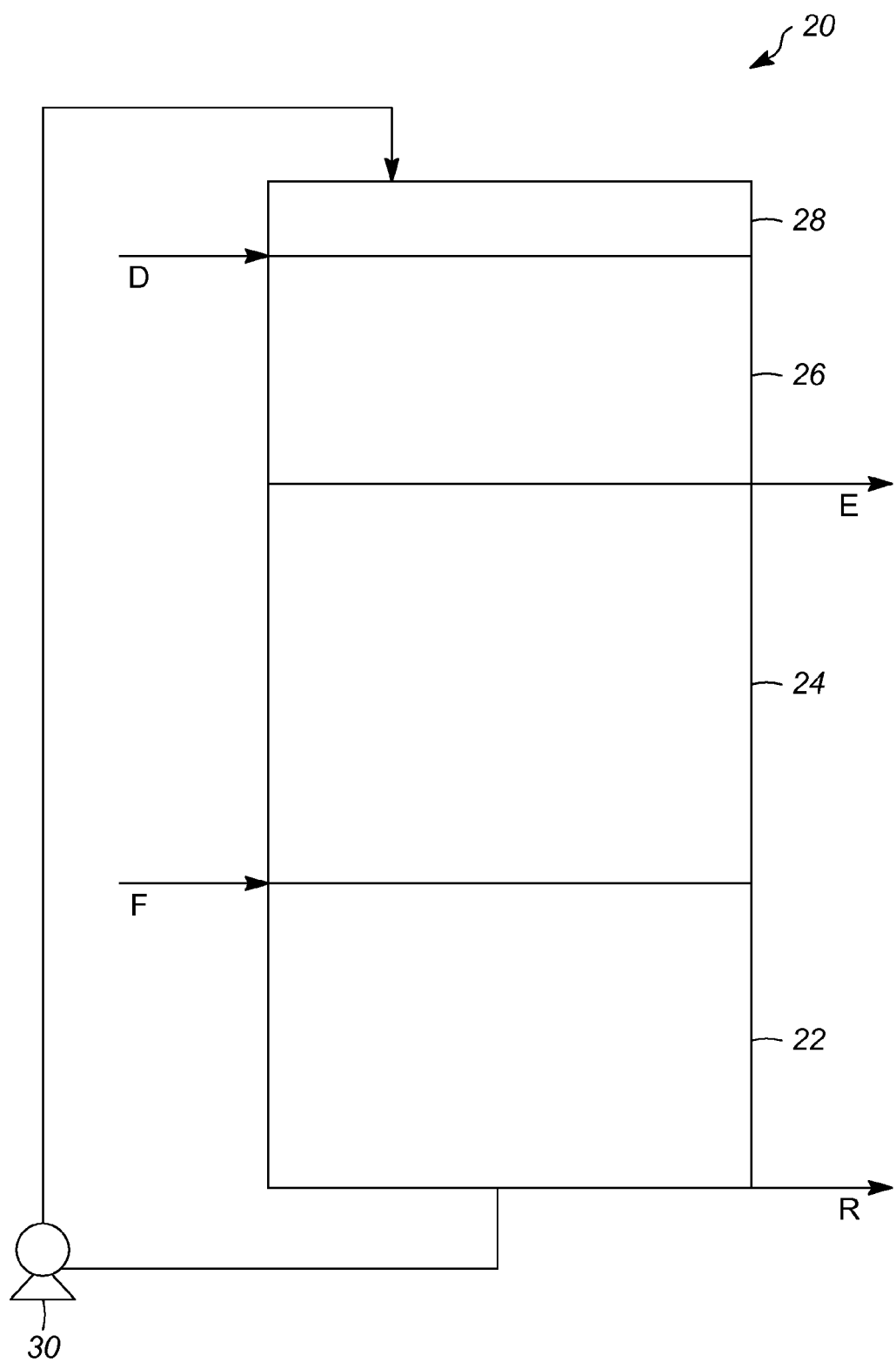
FIG. 3 is a simplified illustration of an exemplary four zone adsorbent chamber of an adsorptive separation unit containing the binderless BaKX zeolitic adsorbent according to an exemplary embodiment of the present invention.

In the simulated moving bed adsorptive separation process, these steps are performed in separate zones (as hereinafter described) within adsorbent beads, i.e. particles, retained in one or more adsorption chambers. FIG. 3 shows a simplified four-zone adsorbent chamber 20. In the simulated moving bed adsorptive separation process 40, the adsorption and displacement are continuously taking place using the continuous flow of feed stream F and desorbent stream D and allows continuous production of an extract stream E and a raffinate stream R. In such a system, it is the progressive movement of multiple liquid access points down an adsorbent chamber that simulates the upward movement of adsorbent contained in the adsorbent chamber 20.

A number of specially defined terms are used in describing the simulated moving bed processes. The term "feed stream" or "feed inlet stream" indicates a stream in the process through which a feed mixture to be separated passes to the adsorbent. The feed mixture comprises one or more extract components and one or more raffinate components. An "extract component" is a compound or type of compound that is more selectively retained by the adsorbent while a "raffinate component" or "raffinate material" is a compound or type of compound that is less selectively retained. Here, the feed mixture comprises mixed xylenes. As stated previously, as used herein "mixed xylenes" refers to a mixture of C8 aromatic isomers that includes ethyl benzene, para-xylene, meta-xylene, and ortho-xylene. Accordingly, ethyl benzene, meta-xylene, and ortho-xylene from the feed stream are raffinate components while para-xylene is the extract component. The term "desorbent" shall mean generally a material capable of displacing an extract component. A suitable desorbent for the process described herein comprises para-diethylbenzene (PDEB), but the invention is not so limited. Other suitable desorbents include, e.g. toluene and tetralin. The term "desorbent stream" or "desorbent inlet stream" indicates the stream through which desorbent passes to the adsorbent. The term "raffinate stream" or "raffinate outlet stream" means a stream through which most of the raffinate components are removed from the adsorbent. The composition of the raffinate stream can vary from about 100% desorbent to essentially 100% raffinate components. The term "extract stream" or "extract outlet stream" shall mean a stream through which an extract material, which has been displaced by desorbent, is removed from the adsorbent. The composition of the extract stream can vary from about 100% desorbent to essentially 100% extract components.

The term "selective pore volume" of the adsorbent is defined as the volume of the adsorbent which selectively retains extract components from the feed stream. The term "non-selective void volume" of the adsorbent is the volume of the adsorbent that does not selectively retain extract components from the feed stream. This volume includes the cavities of the adsorbent, which are capable of retaining raffinate components, and the interstitial void spaces between adsorbent particles. The selective pore volume and the non-selective void volume are generally expressed in volumetric quantities and are of importance in determining the proper flow rates of fluid required to be passed into an operational zone for efficient operations to take place for a given quantity of adsorbent.

When adsorbent "passes" into an operational zone (hereinafter defined and described) its non-selective void volume together with its selective pore volume carries fluid into that zone. The non-selective void volume is utilized in determining the amount of fluid that should pass into the same zone in a countercurrent direction to the adsorbent to displace the fluid present in the non-selective void volume. If the fluid flow rate passing into a zone is smaller than the non-selective void volume rate of adsorbent material passing into that zone, there is a net entrainment of liquid into the zone by the adsorbent. Since this net entrainment is a fluid present in a non-selective void volume of the adsorbent, in most instances, it comprises less selectively retained feed components.

In the simulated moving bed process, four primary liquid access points are active at any one time: the feed inlet stream, desorbent inlet stream, raffinate outlet stream, and extract outlet stream access points. Optionally, additional access points may be used if needed, e.g. for flushing as is well known in the art. Coincident with this simulated upward movement of the solid adsorbent is the movement of the liquid occupying the void volume of the adsorbent. So that countercurrent contact is maintained, a liquid flow down the adsorbent chamber may be provided by a pump. As an active liquid access point moves through a cycle, that is, from the top of the adsorbent chamber to the bottom, the chamber circulation pump 30 moves through different zones which require different flow rates. A programmed flow controller (not shown) may be provided to set and regulate these flow rates.

The active liquid access points effectively divide the adsorbent chamber into separate zones, each of which has a different function. In this embodiment of the process, three separate operational zones typically are present in order for the process to take place, although in some instances an optional fourth zone may be used.

Referring to FIG. 3, an adsorption zone 22 is defined as the adsorbent located between the feed inlet stream and the raffinate outlet stream. In this zone, the feed stream contacts the adsorbent, an extract component is retained, and a raffinate stream is withdrawn. Since the general flow through zone 22 is from the feed stream which passes into the zone to the raffinate stream which passes out of the zone, the flow in this zone is considered to be in a downstream direction when proceeding from the feed inlet to the raffinate outlet streams.

Immediately upstream with respect to fluid flow in adsorption zone 22 is a purification zone 24. The purification zone 24 is defined as the adsorbent between the extract outlet stream and the feed inlet stream. The basic operations taking place in zone 24 are the displacement from the non-selective void volume of the adsorbent of any raffinate component carried into zone 24 by the shifting of adsorbent into this zone and the displacement of any raffinate component retained within the selective pore volume of the adsorbent. Purification is achieved by passing a portion of extract stream material leaving a desorption zone 26 (discussed hereinafter) into zone 24 at the zone 24 upstream boundary to effect the displacement of raffinate material. The flow of liquid in zone 24 is in a downstream direction from the extract outlet stream to the feed inlet stream. The para-xylene is further enriched as the desorbent pushes the raffinate components from the non-selective void volume of the adsorbent and the selective void volume into zone 22.

Immediately upstream of zone 24 with respect to the fluid flowing in zone 24 is the desorption zone 26. The desorption zone 26 is defined as the adsorbent between the desorbent inlet and the extract outlet streams. The function of the desorption zone 26 is to allow a desorbent which passes into this zone to displace the extract component which was retained in the adsorbent during a previous contact with the feed stream in zone 22 in a prior cycle of operation. The flow of fluid in zone 26 is essentially in the same direction as that of zones 22 and 24.

In an optional exemplary embodiment, a buffer zone, zone 28, may be utilized. This zone, defined as the adsorbent between the raffinate outlet stream and the desorbent inlet stream, if used, is located immediately upstream with respect to the fluid flow to zone 26. Zone 28 can be utilized to conserve the amount of desorbent utilized in the desorption step since a portion of the raffinate stream which is removed from zone 22 can be passed directly into zone 28 to displace present desorbent and cause it to flow to the desorption zone 26. Zone 28 contains enough desorbent so that raffinate material present in the raffinate stream passing from zone 22 into zone 28 can be prevented from passing into zone 26, thereby contaminating the extract stream removed from zone 24. In the instances in which optional zone 28 is not utilized, the raffinate stream flowing from zone 22 to zone 28 must be carefully monitored so that the flow directly from zone 22 to zone 26 can be stopped when there is an appreciable quantity of raffinate material present in the raffinate stream passing from zone 22 into zone 26 to prevent the extract outlet stream from being contaminated.

EXAMPLES

The following are examples of binderless BaKX zeolitic adsorbents having various formulations (Examples A-J). Properties of the formulations and test results relative to Comparative Formulations A and F are summarized in TABLE 1 below. The examples are provided for illustration purposes only, and are not meant to limit the various embodiments of the present invention in any way. Formulations A-J were prepared according to the steps described above using 13X zeolite powder with a silica:alumina molar ratio of about 2.5 and EPK kaolin clay from Imerys as the binder.

Pulse/dynamic performance evaluation experiments, known in the art, were conducted with a particular feed mixture to measure adsorptive capacity and selectivity of the various formulations. A dynamic testing apparatus consisting of an adsorbent chamber of approximately 70 cc volume having inlet and outlet portions at opposite ends of the chamber was employed. The chamber was contained within a temperature control means and, in addition, pressure control equipment was used to operate the chamber at a constant predetermined pressure. Chromatographic analysis equipment was attached to the outlet line of the chamber and used to analyze, "on-stream", the effluent stream leaving the adsorbent chamber.

A pulse test, performed using this apparatus and the following general procedure, was used to determine selectivities, mass transfer, and other data for the various adsorbent formulations. The adsorbent was filled to equilibrium with para-diethylbenzene by flowing the desorbent through the adsorbent chamber. At a convenient time, a pulse of feed containing known concentrations of a nonadsorbed paraffinic tracer (n-nonane) and of the particular aromatic isomers (para-, ortho-, and meta-xylene, and ethylbenzene) diluted in the desorbent was injected for a duration of several minutes. After injection, desorbent flow was resumed, and the tracer and the aromatic isomers were eluted as in a liquid-solid chromatographic operation. The effluent was analyzed by on-stream chromatographic equipment and traces of the envelopes of corresponding component peaks were developed. Alternatively, effluent samples could have been collected periodically and later analyzed separately by gas chromatography.

The dynamic test (also known as a breakthrough test) was also performed to determine adsorption capacity, para-xylene to para-diethylbenzene selectivity, and mass transfer characteristics. The adsorbent was first filled to equilibrium with toluene containing a known concentration of a nonadsorbed paraffinic tracer (n-nonane) by flowing toluene through the adsorbent chamber. At a convenient time, the flow was switched to a mixture of para-xylene and para-diethylbenzene flow. Over time, para-xylene and para-diethylbenzene broke through. The adsorption capacity was determined by the difference in the total amount of para-xylene and para-diethylbenzene that was fed to the adsorbent chamber minus the total amount of para-xylene and paraethylbenzene that eluted.

From information derived from the chromatographic traces, adsorbent performance was rated in terms of capacity index for an extract component, and selectivity for one isomer with respect to another and to the desorbent. The higher the adsorbent's capacity for an extract component, the better is the adsorbent. Increased capacity of a particular adsorbent makes it possible to reduce the amount of adsorbent needed to separate the extract component for a particular charge rate of feed mixture. A reduction in the amount of adsorbent required for a specific adsorptive separation reduces the cost of the separation process. The good initial capacity of the adsorbent should be maintained during actual use in the separation process over some economically desirable life.

Selectivity (B) for an isomer can be expressed not only for one feed mixture component as compared to another, but can also be expressed between any feed mixture component and the desorbent. Relative selectivity is shown in the equation below: Selectivity (B)=[vol. percent C/vol. percent D]$_A$/[vol. percent C/vol. percent D]$_U$ where C and D are two components of the feed stream represented in volume percent and the subscripts A and U represent the adsorbed and unadsorbed phases, respectively. Thus $C_A$ and $C_U$ represent the concentrations of component C in the adsorbent (adsorbed phase) and feed stream (unadsorbed phase), respectively, and $D_A$ and $D_U$ represent the concentrations of component D in the adsorbent and the feed stream, respectively. Equilibrium conditions are reached when the feed stream passing over a bed of adsorbent does not change composition after contacting the bed of adsorbent. In other words, equilibrium conditions are reached when there is no net transfer of material occurring between the unadsorbed (feed stream) and adsorbed phases (adsorbent).

Where selectivity of two components approaches 1.0, there is no preferential adsorption of one component by the adsorbent with respect to the other; that is, they are both adsorbed (or nonadsorbed) to about the same degree with respect to each other. As the selectivity (B) becomes less than or greater than 1.0, there is a preferential adsorption by the adsorbent for one component with respect to the other. When comparing the selectivity by the adsorbent of one component C over component D, a (B) larger than 1.0 indicates preferential adsorption of component C within the adsorbent. A (B) less than 1.0 would indicate that component D is preferentially adsorbed, leaving an unadsorbed phase richer in component C and an adsorbed phase richer in component D. While separation of an extract component from a raffinate component is theoretically possible when the selectivity of the adsorbent for the extract component with respect to the raffinate component just exceeds a value of 1.0, it is preferred that such selectivity have a value approaching or exceeding 2. The higher the selectivity, the easier the separation is to perform. Higher selectivities permit a smaller amount of adsorbent to be used in the process. Ideally, the desorbent should have a selectivity equal to about 1 or less than 1 with respect to all extract components so that all of the extract components can be extracted as a class and all raffinate components rejected into the raffinate stream.

Based on acceptable data from these experiments, equilibrium SMB process modeling was developed to predict process performance and adsorbent productivity of the binderless BaKX adsorbent in accordance with exemplary embodiments of the present invention. The results of this modeling are summarized in TABLE 1, which compares the feed rate and D/F ratio as a percentage relative to a Base Case. Results for Formulations B-E are reported relative to Formulation A and Formulations G-J are reported relative to Formulation F. More detailed information about process modeling for calculating productivity is provided in Marco Mazzotti, etc. "Robust Design of Countercurrent Adsorption Separation Processes: 2. Multicomponent Systems", AIChE Journal, November 1994, Vol. 40, No. 11.

The D/F ratio (desorbent/feed ratio) is an important process parameter that has a strong impact on the operating cost of an adsorptive separation process. The D/F ratio is the ratio of the flow rate of the desorbent to the flow rate of the feed stream in the simulated moving bed separation process. The D/F ratio translates into the amount of desorbent required to process a given amount of feed stream. The lowest D/F ratio is preferred. The lower the D/F, the less desorbent is required to displace the adsorbed para-xylene from the adsorbent, i.e., there is a significant reduction of desorbent demand (relative to feed processed). This translates to reduced operating costs, in addition to significantly improving productivity of the adsorptive process. While it is desirable to lower the D/F ratio, it is important that the amount of feed that can be processed not be affected.

TABLE 1

| Formulation | Zeolite, wt % | Kaolin clay binder, wt % | CMC, wt % | K, wt % | Ba, wt % | Na, wt % | Feed, % | D/F, % |
|---|---|---|---|---|---|---|---|---|
| A | 86 | 14 | 2 | 0.3 | 32.9 | 0.1 | Base | Base |
| B | 86 | 14 | 2 | 0.5 | 33.0 | 0.1 | 1.01 | 0.95 |
| C | 86 | 14 | 2 | 0.7 | 32.6 | 0.1 | 1.03 | 0.95 |
| D | 86 | 14 | 2 | 0.9 | 32.3 | 0.1 | 1.00 | 0.91 |
| E | 86 | 14 | 2 | 1.2 | 31.3 | 0.1 | 1.00 | 0.92 |
| F | 88 | 12 | 1 | 0.2 | 33.2 | 0.1 | Base | Base |
| G | 88 | 12 | 1 | 0.5 | 32.7 | 0.1 | 1.01 | 1.00 |
| H | 88 | 12 | 1 | 0.7 | 31.8 | 0.1 | 1.00 | 0.97 |
| I | 88 | 12 | 1 | 0.9 | 32.1 | 0.1 | 1.00 | 0.95 |
| J | 88 | 12 | 1 | 1.3 | 31.5 | 0.1 | 0.98 | 0.94 |

From the foregoing, it is to be appreciated that the exemplary embodiments of the binderless BaKX zeolitic adsorbent described herein increase the productivity of the adsorptive separation process and decrease operating costs by using less desorbent at essentially the same feed rate. The adsorbent requires less desorbent circulation per ton of product compared to prior art adsorbents. Lower desorbent circulation means lower utility consumption per ton of product. Higher productivity means more para-xylene can be produced with a fixed adsorbent volume.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way.

The invention claimed is:

1. A binderless BaKX zeolitic adsorbent comprising:
    a first Zeolite X having a silica to alumina molar ratio of from about 2.0 to about 3.0;
    a binder-converted Zeolite X wherein a ratio of the binder-converted Zeolite X to the first Zeolite X ranges from about 10:90 to about 20:80 by weight; and
    barium and potassium at cationic exchangeable sites within the binderless BaKX zeolitic adsorbent; wherein potassium ranges from about 0.9 wt % to about 1.5 wt % of the binderless BaKX zeolitic adsorbent, and barium ranges from about 30 wt % to about 34 wt % of the binderless BaKX zeolitic adsorbent.

2. The binderless BaKX zeolitic adsorbent of claim 1, wherein the ratio of the binder-converted Zeolite X to the first Zeolite X ranges from about 14:86 to about 18:82 by weight.

3. The binderless BaKX zeolitic adsorbent of claim 1, wherein the potassium ranges from more than 0.9 wt % to about 1.25 wt % of the binderless BaKX zeolitic adsorbent.

4. The binderless BaKX zeolitic adsorbent of claim 1, wherein the potassium ranges from 0.95 wt % to about 1.15 wt % of the binderless BaKX zeolitic adsorbent.

5. The binderless BaKX zeolitic adsorbent of claim 1, wherein the barium ranges from about 31 wt % to about 33 wt % of the binderless BaKX zeolitic adsorbent.

6. The binderless BaKX zeolitic adsorbent of claim 1, wherein the first Zeolite X has a silica to alumina molar ratio of from about 2.35 to about 2.65.

7. The binderless BaKX zeolitic adsorbent of claim 1, wherein the binder-converted Zeolite X has a silica to alumina molar ratio of from about 2.0 to about 2.2.

8. The binderless BaKX zeolitic adsorbent of claim 1, wherein a sodium content of the binderless BaKX zeolitic adsorbent is less than 0.15 wt % of the binderless BaKX zeolitic adsorbent.

9. The binderless BaKX zeolitic adsorbent of claim 1, wherein LOI at 900° C. comprises about 4 wt % to about 7 wt % of the binderless BaKX zeolitic adsorbent.

10. The binderless BaKX zeolitic adsorbent of claim 1, wherein the ratio of the binder-converted Zeolite X to the first Zeolite X ranges from about 14 to 86 to about 18 to 82 by weight; potassium ranges from 0.95 wt % to about 1.15 wt % of the binderless BaKX zeolitic adsorbent; barium ranges from about 31 wt % to about 33 wt % of the binderless BaKX zeolitic adsorbent; the first Zeolite X has a silica to alumina molar ratio of from about 2.3 to about 2.7; the binder-converted Zeolite X has a silica to alumina molar ratio of from about 2.0 to about 2.2; and a sodium content of the binderless BaKX zeolitic adsorbent is less than about 0.15 wt % of the binderless BaKX zeolitic adsorbent.

11. The binderless BaKX zeolitic adsorbent of claim 1, wherein the binderless BaKX zeolitic adsorbent has a combined macro-pore and meso-pore volume between 0.5 cc/g and 0.35 cc/g.

12. A method for producing a binderless BaKX zeolitic adsorbent comprising:
   forming agglomerates having ion-exchangeable sites, the agglomerates formed from Zeolite X having a silica to alumina molar ratio of from about 2.0 to about 3.0, a kaolin clay binder, and carboxymethyl cellulose;
   activating the agglomerates to convert the kaolin clay binder to meta-kaolin clay binder;
   dissipating the carboxymethyl cellulose;
   converting the meta-kaolin clay binder into binder-converted Zeolite X;
   exchanging the ion-exchangeable sites with barium and potassium to provide the binderless BaKX zeolitic adsorbent having potassium in an amount ranging from about 0.9 wt % to about 1.5 wt % of the binderless BaKX zeolitic adsorbent, and barium in an amount ranging from about 30 wt % to about 34 wt % of the binderless BaKX zeolitic adsorbent; and
   drying the binderless BaKX zeolitic adsorbent.

13. The method of claim 12, wherein the carboxymethyl cellulose is dissipated in the activating step.

14. The method of claim 13, wherein the step of forming agglomerates comprises combining the Zeolite X, the kaolin clay binder, and carboxymethyl cellulose, wherein the proportion of the Zeolite X to the kaolin clay binder ranges from about 80 to 20 to about 90 to 10 by weight, and the amount of carboxymethyl cellulose is not more than about 5 wt % of the combined weight of the kaolin clay binder and the Zeolite X.

15. The method of claim 12, wherein the step of forming agglomerates comprises forming adsorbent beads.

16. The method of claim 12, wherein the step of forming agglomerates comprises forming agglomerates with Zeolite X having a silica to alumina molar ratio of from about 2.3 to about 2.7.

17. The method of claim 12, wherein the step of exchanging the ion-exchangeable sites comprises reducing the amount of sodium at cationic exchangeable sites to provide the binderless BaKX zeolitic adsorbent having a sodium content of less than about 0.15 wt % of the binderless BaKX zeolitic adsorbent.

18. The method of claim 12, wherein the step of activating the agglomerates comprises heating the agglomerates to a temperature from about 625° C. to about 700° C., and the step of converting the meta-kaolin clay binder into binder-converted Zeolite X comprises caustic digesting the meta-kaolin clay binder with an aqueous alkali metal hydroxide solution.

19. An adsorptive separation process for separating para-xylene from a feed mixture comprising at least one other C8 aromatic isomer, the process comprising:
   contacting the feed mixture with a binderless BaKX zeolitic adsorbent comprised of a first Zeolite X portion having a silica to alumina molar ratio of from about 2.0 to about 3.0; a binder-converted Zeolite X portion; and barium and potassium at cationic exchangeable sites within the binderless BaKX zeolitic adsorbent, wherein potassium ranges from about 0.9 wt % to about 1.5 wt % of the binderless BaKX zeolitic adsorbent, and barium ranges from about 30 wt % to about 34 wt % of the binderless BaKX zeolitic adsorbent;
   causing para-xylene to be adsorbed on the binderless BaKX zeolitic adsorbent;
   removing a less selectively adsorbed portion of the feed mixture from contact with the binderless BaKX zeolitic adsorbent as a raffinate stream; and
   recovering the para-xylene from the binderless BaKX zeolitic adsorbent by desorption with a desorbent.

20. The process of claim 19, wherein the desorbent comprises para-diethylbenzene.

21. The process of claim 19, wherein a ratio of the binder-converted Zeolite X portion to the first Zeolite X portion ranges from about 10:90 to about 20:80 by weight.

* * * * *